US00RE34865E

United States Patent [19]

Adam et al.

[11] E Patent Number: Re. 34,865

[45] Reissued Date of Patent: Feb. 21, 1995

[54] CEPHALOSPORIN DERIVATIVES

[75] Inventors: Friedhelm Adam, Tacoma, Wash.; Jürgen Blumbach, Niedernhausen, Germany; Walter Dürckheimer, Hattersheim am Main, Germany; Gerd Fischer, Frankfurt am Main, Germany; Burghard Mencke, Holzappel, Germany; Dieter Isert, Eschborn, Germany; Gerhard Seibert, Darmstadt, Germany

[73] Assignee: Hoechst Aktiengesellschaft, Frankfurt am Main, Germany

[21] Appl. No.: 978,980

[22] Filed: Nov. 19, 1992

Related U.S. Patent Documents

Reissue of:

[64] Patent No.: 5,100,887
Issued: Mar. 31, 1992
Appl. No.: 555,807
Filed: Jul. 23, 1990

U.S. Applications:

[63] Continuation of Ser. No. 310,437, Feb. 15, 1989, abandoned.

[30] Foreign Application Priority Data

Feb. 17, 1988 [DE] Germany ..... 3804841.8

[51] Int. Cl.[6] ..... A61K 31/545; C07D 501/32

[52] U.S. Cl. ..... 514/202; 540/222

[58] Field of Search ..... 540/222; 514/202

[56] References Cited

U.S. PATENT DOCUMENTS

| | | | |
|---|---|---|---|
| 4,098,888 | 6/1978 | Ochiai et al. | 424/246 |
| 4,203,899 | 5/1980 | Ochiai et al. | 548/194 |
| 4,205,180 | 5/1980 | Ochiai et al. | 560/168 |
| 4,264,595 | 4/1981 | Numata et al. | 424/246 |
| 4,278,793 | 7/1981 | Dürckheimer et al. | 544/27 |
| 4,283,396 | 8/1981 | Heymes et al. | 424/246 |
| 4,298,606 | 11/1981 | Ochiai et al. | 424/246 |
| 4,355,160 | 10/1982 | Ochiai et al. | 544/27 |
| 4,409,215 | 10/1983 | Takaya et al. | 424/246 |

(List continued on next page.)

FOREIGN PATENT DOCUMENTS

| | | |
|---|---|---|
| 0034536A2 | 2/1981 | European Pat. Off. . |
| 0034536B1 | 2/1981 | European Pat. Off. . |
| 0029557A2 | 3/1981 | European Pat. Off. . |
| 0049119A2 | 4/1982 | European Pat. Off. . |

(List continued on next page.)

OTHER PUBLICATIONS

Chemical Abstracts vol. 117: 103648 (1992).

Chemical Abstracts, vol. 97, 162705p (1982).

In Vivo Evaluation of Tigemonam, a Novel Oral Monobactam, Junius M. Clark et al., Antimicrobial Agents and Chemotherapy, vol. 31, No. 2, Feb. 1987, pp. 226–229.

Pharmacokinetic and In Vivo Studies with Azithromy- (List continued on next page.)

*Primary Examiner*—Nicholas Rizzo

*Attorney, Agent, or Firm*—Finnegan, Henderson, Farabow, Garrett & Dunner

[57] ABSTRACT

Cephemcarboxylic acid esters of the general formula

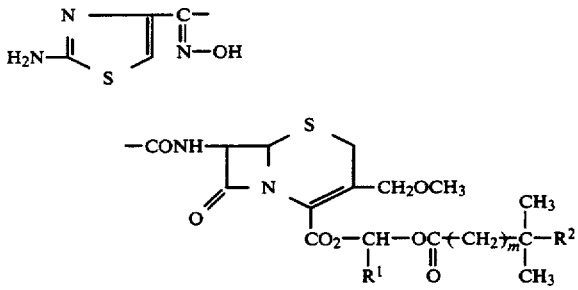

pharmaceutical preparations which are active against bacterial infections, which contain such cephem derivatives, a process for the preparation of the cephem derivatives and the pharmaceutical preparations, and also the use of the cephem derivatives for combating bacterial infections.

3 Claims, No Drawings

U.S. PATENT DOCUMENTS

| | | | |
|---|---|---|---|
| 4,462,999 | 7/1984 | Takaya et al. | 424/246 |
| 4,483,855 | 11/1984 | Nakao et al. | 424/246 |
| 4,486,425 | 12/1984 | Nakao et al. | 424/246 |
| 4,514,565 | 4/1985 | Ochiai et al. | 544/25 |
| 4,668,783 | 5/1987 | Ochiai et al. | 540/222 |
| 4,904,652 | 2/1990 | Takaya et al. | 514/206 |
| 4,912,212 | 3/1990 | Ochiai et al. | 540/227 |
| 4,973,684 | 11/1990 | Ochiai et al. | 540/222 |
| 4,992,431 | 3/1991 | Heymes et al. | 514/202 |
| 5,026,695 | 6/1991 | Takaya et al. | 514/202 |
| 5,063,224 | 11/1991 | Mosher et al. | 514/202 |

FOREIGN PATENT DOCUMENTS

| | | |
|---|---|---|
| 0134420A1 | 3/1985 | European Pat. Off. . |
| 2556736A1 | 6/1976 | Germany . |
| 2560398C2 | 9/1983 | Germany . |

OTHER PUBLICATIONS cin (CP-62,993), a New Macrolide with an Extended Half-Life and Excellent Tissue Distribution, Girard et al., Antimicrobial Agents and Chemotherapy, vol. 31, No. 12, Dec. 1987, pp. 1948-1954.

The Relationships of Absorption Characteristics and Gastrointestinal Side Effects of Oral Antimicrobial Agents, Grossman, Clinical Therapeutics, vol. 13, No. 1, pp. 189-193 (1991).

Uptake of the cephalosporin, cephalexin, by a dipeptide transport carrier in the human intestinal cell line, Caco-2, Dantzig et al., Biochimica et Biophysica Acta, 1027, pp. 211-217 (1990).

Stereochemical Considerations in Drug Absorption, Disposition and Pharmacokinetics, Hutt, Drug Chirality, 24th and 25th Oct., 1990.

Studies on Orally Active Cephalosporin Esters. IV.[1]), Miyauchi et al., Chem. Pharm. Bull. 32(12), pp. 3272-3276 (1989).

Studies on Orally Active Cephalosporin Esters. II.[1]), Miyauchi et al., Chem. Pharm. Bull. 37(9), pp. 2369-2374 (1989.

Synthesis and Mechanisms of Decomposition of Some Cephalosporin Prodrugs, Saab et al., Journal of Pharmaceutical Sciences, vol. 79, No. 9, (1990).

Orally Active 1-(Cyclohexyloxycarbonyloxy)Alkyl Ester Prodrugs of Cefotiam Nishimura et al., The Journal of Antibiotics, vol. XL, No. 1, pp. 81-90 (1986).

Angewandte Chemie, vol. 24, No. 3, Mar. 1985, pp. 180-202.

Pharmacokinetics of FK482, A New Orally Active Cephalosporin, in Animals, Sakamoto et al., The Journal of Antibiotics, vol. XLI, No. 12, pp. 1896-1905 (1988).

CEPHALOSPORIN DERIVATIVES

Matter enclosed in heavy brackets [ ] appears in the original patent but forms no part of this reissue specification; matter printed in italics indicates the additions made by reissue.

This application is a continuation of application Ser. No. 07/310,437, filed Feb. 15, 1989, now abandoned.

The invention relates to novel cephalosporin derivatives which are particularly suitable for oral administration, a process for their preparation and pharmaceutical formulations containing such compounds.

Although many clinically relevant cephalosporins with a broad antibacterial spectrum have been developed, most of them are suitable only for parenteral administration, since they are absorbed only very inadequately, if at all, following oral administration. In many cases, however, it is desirable to give the patient highly active antibiotics in oral form.

The cephalosporin antibiotics known to date do not meet all the requirements which have to be imposed on such a medicament, that is to say a high antibacterial activity against Gram-positive (specifically Staphylococci) and Gram-negative pathogens and at the same time a good absorption in the gastrointestinal tract.

In some cases, it has been possible to increase the absorption of a cephalosporin in the gastrointestinal tract by esterification of the 4-carboxyl group. Since the cephalosporin esters as a rule have no antibiotic activity in themselves, the ester component must be chosen so that after absorption, the ester is split back again into the cephalosporin with a free carboxyl group rapidly and completely by endogenous enzymes, such as esterases.

The degree of enteral absorption of cephalosporins depends decisively on the chemical structure of the cephalosporin and the particular ester component. Even small structural variations on the cephalosporin basic skeleton or in the ester component can influence the absorption. The discovery of suitable components is purely empirical.

Thus, for example, the introduction of an acid substituent into the 7 β-side chain of aminothiazolyl-cephalosporins, such as, for example, in cefixime, leads to a compound which can be absorbed enterally, whereas compounds with neutral side chains, such as, for example, in cefuroxime, are absorbed enterally only in the form of prodrug esters. The dose/effect relationship is thereby often non-linear and the therapeutic serum levels achieved are not satisfactory. Other esters from the aminothiazolyl-cephalosporin series are mentioned, for example, in European patents 29,557, 34,536, 49,119 and 134,420.

By in vivo studies carried out systematically on various animal species, we have now found a narrow group of ceph-3-em-4-carboxylic acid esters which can be administered orally, have a sufficient chemical stability and due to a balanced lipid- and water-solubility are absorbed rapidly and in a therapeutically substantial degree in the gastrointestinal tract.

The invention accordingly relates to cephemcarboxylic acid esters of the general formula I

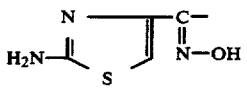

(I)

-continued

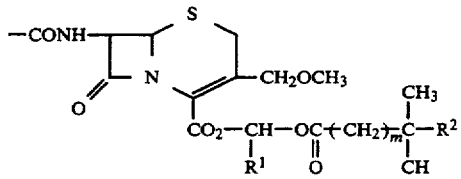

in which m denotes 0 or 1, $R^1$ denotes hydrogen or methyl and $R^2$ denotes $C_1$–$C_6$-alkyl, $C_2$–$C_6$-alkenyl, $C_2$–$C_6$-alkynyl or the group $$-(CH_2)_n-OR^3$$

in which n stands for 0 or 1 and $R^3$ has the meaning of $C_1$–$C_6$-alkyl, which can also be further substituted by phenyl, or of $C_3$–$C_4$-alkenyl, in which the HO group is in the syn-position and, if m is 0 or $R^1$ is hydrogen, $R^2$ cannot be methyl, and physiologically tolerated acid addition salts thereof.

In the case where m is 0 and $R^1$ is hydrogen or methyl, the following meanings of $R^2$ are possible:

$C_1$–$C_6$-alkyl, preferably $C_1$–$C_4$-alkyl, such as, for example, methyl, ethyl, propyl, isopropyl, butyl or sec.-butyl, preferably methyl or methyl, in particular ethyl, and in the case where $R^1$ is hydrogen, $R^2$ cannot be methyl, $C_2$–$C_6$-alkenyl, preferably $C_2$–$C_4$-alkenyl, such as, for example, vinyl, propenyl or 2-butenyl, preferably vinyl, $C_2$–$C_6$-alkynyl, preferably $C_3$–$C_4$-alkynyl, in particular propargyl, or the group $$-(CH_2)_n-OR^3$$

in which n can be 0 or 1 and $R^3$ denotes $C_1$–$C_6$-alkyl, preferably $C_1$–$C_4$-alkyl, such as, for example, methyl, ethyl, propyl, isopropyl, butyl or sec.-butyl, preferably methyl or ethyl, it also being possible for the alkyl groups to be further substituted by phenyl, or $C_3$–$C_4$-alkenyl, such as, for example, allyl or methallyl, preferably allyl.

If m denotes 0, compounds of the general formula I in which $R^1$ is hydrogen and $R^2$ is ethyl or vinyl, preferably ethyl, or $R^1$ stands for methyl and $R^2$ stands for methyl or ethyl, preferably methyl, are of particular interest.

If m=1, possible meanings of $R^1$, $R^2$ and n are the same as those given above. However, compounds in which $R^1$ stands for hydrogen or methyl, preferably hydrogen, and $R^2$ stands for $C_1$–$C_4$-alkyl, such as, for example, methyl, ethyl, propyl, isopropyl, butyl or sec.-butyl, preferably methyl, are particularly preferred.

Possible physiologically tolerated acid addition salts are the salts known for cephalosporin antibiotics, such as, for example, the hydrochloride, sulfate, maleate, citrate, acetate for formate. They are prepared in a manner which is known per se by bringing the components together in an aqueous or organic solvent or a suitable solvent mixture. If $R^1=CH_3$, the compounds of the general formula I have a chiral center in the ester part. If racemic compounds of the general formula IIi are used, the cephemcarboxylic acid esters of the general formula I are in the form of a mixture of two diastereomers, which can be resolved into the two individual components by known methods.

The invention furthermore relates to a process for the preparation of cephemcarboxylic acid esters of the general formula:

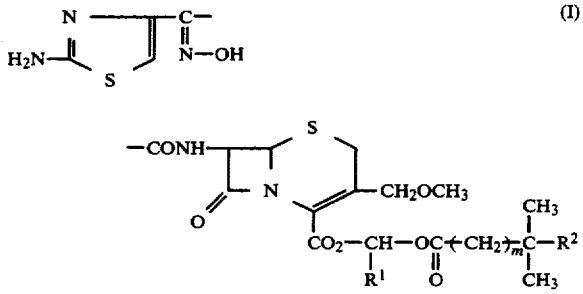

(I)

in which m denotes 0 or 1, $R^1$ denotes hydrogen or methyl and $R^2$ denotes $C_1$–$C_6$-alkyl, $C_2$–$C_6$-alkenyl, $C_2$–$C_6$-alkynyl or the group $-(CH_2)_n-OR^3$ in which n stands for 0 or 1 and $R^3$ has the meaning of $C_1$–$C_6$-alkyl, which can also be further substituted by phenyl, or of $C_3$–$C_4$-alkenyl, in which the HO group is in the syn-position and, if m is 0 or $R^1$ is hydrogen. $R^2$ cannot be methyl, and physiologically tolerated acid addition salts thereof, which comprises (a) reacting a compound of the formula II

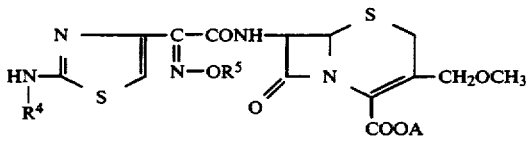

(II)

in which $R^4$ stands for an amino-protective group, $R^5$ stands for a group which can easily be split off and A stands for a cation, with a compound of the general formula III

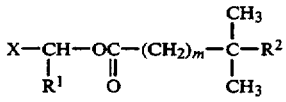

(III)

in which $R^1$, $R^2$ and m have the above meaning and X stands for a leaving group, to give the ester of the general formula IV

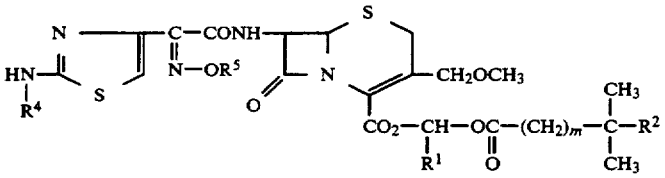

(IV)

and removing the groups $R^4$ and $R^5$ in a manner which is known per se, or (b) reacting a compound of the general formula V

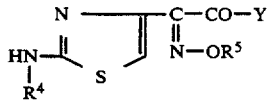

(V)

in which $R^4$ and $R^5$ have the above meaning and Y stands for an activating group, with a compound of the general formula VI

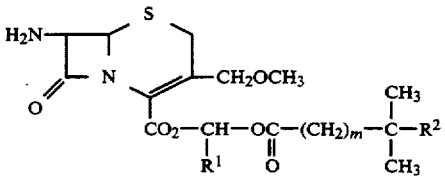

(VI)

in which $R^1$, $R^2$ and m have the above meaning, or with a salt of this compound, to give a compound of the general formula IV and splitting off the groups $R^4$ and $R^5$ in a manner which is known per se, or (c) reacting a compound of the general formula VII

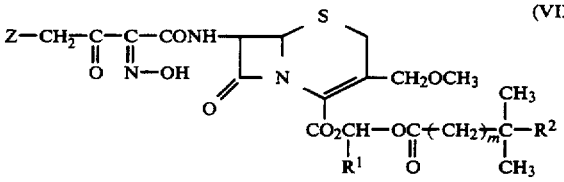

(VII)

in which Z stands for halogen and $R^1$, $R^2$ and m have the above meaning, with thiourea to give compounds of the general formula I and—if desired—converting the resulting compounds into a physiologically tolerated acid addition salt.

In the general formulae, II, IV and V, $R^4$ stands for an amino-protective group which is known from peptide and cephalosporin chemistry, preferably formyl, chloroacetyl, bromoacetyl, trichloroacetyl, benzyloxycarbonyl, tert.-butoxycarbonyl or trityl, and $R^5$ stands for a group which can easily be split off and is likewise known from peptide and cephalosporin chemistry, preferably benzhydryl, trityl, tetrahydropyranyl or 1-methoxy-1-methyl-ethyl. Trityl is particularly preferred for $R^4$, and trityl and 1-methoxy-1-methyl-ethyl are particularly preferred for $R^5$.

In formula III, X denotes a leaving group which is generally known for esterification reactions, such as, for example, chlorine, bromine, iodine, phenylsulfonyloxy, p-toluene-sulfonyloxy or methylsulfonyloxy, preferably chlorine, bromine or iodine, in particular iodine.

Examples which may be mentioned of bases on which the cation A in the general formula II is based are sodium bicarbonate, potassium bicarbonate, sodium carbonate, potassium carbonate and optionally substituted, alkylated amine bases, such as, for example, trimethylamine, triethylmine, diisopropylamine, ethyldiisopropylamine, N,N-dimethylaniline, N,N-dimethylbenzylamine, 1,5-diazabicyclo[4,3,0]non-5-ene (DBN), 1,8-diazabicyclo[5,4,0]undec-7-ene (DBU), pyridine, picoline or 2,6-dimethylpyridine. Preferred bases are sodium bicarbonate or potassium bicarbonate, sodium carbonate or potassium carbonate, triethylamine, N,N-p-dimethylaniline, DBN or DBU.

Reaction of the free carboxylic acids with these bases gives the salts of the general formula II in which A stands for a cation, such as, for example, sodium or potassium, but also magnesium or calcium or an optionally substituted alkylated ammonium ion, such as, for example, ammonium, trimethylammonium, triethylammonium, tetrabutylammonium, diisopropylammonium, ethyldiisopropylammonium, diazabicyclo-8 0,3,4]nonenium or diazabicyclo[0,4,5]undecenium. Preferred meanings of A are sodium, potassium, triethylammonium, N,N-dimethylanilinium and the DBN and DBU ion.

In compounds of the formula VII, Z stands for a halogen atom, preferably chlorine or bromine.

The reaction of the compounds of the formula II with the compounds of the formula III can be carried out in an organic solvent at about −20° to about +50° C., preferably at about 0° C. to room temperature, Examples of solvents which can be used are ketones, such as, for example, acetone or methylethyl ketone, N,N,-dimethylformamide (DMF), N,N-dimethylacetamide (DMA), N-methylpyrrolidone or dimethylsulfoxide (DMSO). DMF, DMA, N-methylpyrrolidone and DMSO are preferred. DMF is particularly preferred.

The groups $R^4$ and $R^5$ are split off from the resulting compounds of the formula IV in a manner which is known per se from peptide and cephalosporin chemistry, for example with trifluoroacetic acid, dilute hydrochloric acid or preferably with formic acid, with the addition of a little water.

If a compound of the formula V is reacted with a compound of the formula VI, Y represents a group which activates the carboxyl group, such as is known for corresponding reactions from peptide and cephalosporin chemistry, for example a halide, preferably chloride, an activating ester group, for example with 1-hydroxybenzotriazole, or a mixed anhydride, for example with benzenesulfonic acid or toluenesulfonic acid. The activation of the carboxyl group is also possible in a manner which is known from the literature via the addition of a condensing agent, such as, for example, a carbodiimide.

The compound of the general formula VI can be used as such or in the form of a salt, for example the tosylate, hydrochloride or hydriodide, and the use of crystalline salts may be advantageous in respect of the purity of the products.

The reaction of compounds of the formula V with those of the formula VI can be carried out in an organic solvent, such as, for example, methylene chloride, chloroform, acetone, methylethyl ketone, dimethylformamide, dimethylacetamide or water, or in mixture of these solvents.

The acylation reaction can advantageously be carried out at temperatures from about −50° C. to about +50° C., preferably −40° C. to +30° C., if desired in the presence of a base, such as, for example, triethylamine or pyridine. The addition of a base serves to bond the acid component liberated during the condensation.

The cyclization of compounds of the general formula VII with thiourea can be carried out by processes which are known per se, such as are described, for example, in European patent 134,420. For example, it is achieved smoothly at temperatures of about 0° to 30° C., preferably about 5° C., in organic solvents, preferably aprotic polar solvents, such as, for example, dimethylformamide, dimethylacetamide, acetonitrile or acetone.

The starting compounds of the formula III can be prepared in a manner which is known per se by reacting compounds of the general formula

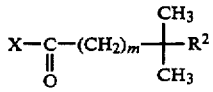

in which m and $R^2$ have the abovementioned meanings are X' stands for a leaving group, with aldehydes of the formula $$R^1—CHO$$

in which $R^1$ has the abovementioned meaning. The preferred meaning of X' is bromine or chlorine. The reaction is advantageously carried out in an organic solvent, such as a halogenated hydrocarbon, for example, methylene chloride or chloroform, in the presence of a catalyst, such as, for example, zinc chloride or aluminum chloride, at a temperature of advantageously −10° C. to +10° C.

Alternatively, the starting compounds of the formula III in which X stands for chlorine can be prepared by reacting a carboxylic acid of the formula

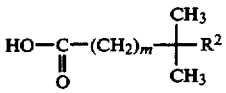

in which $R^2$ and m have the abovementioned meaning and the preparation of which is described in J. Amer. Chem. Soc. 70, page 1153, with a compound of the formula

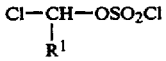

in which $R^1$has the abovementioned meaning and the preparation of which is described in Synthetic Communications 14, page 857, in the presence of a base, such as, for example, sodium carbonate, potassium carbonate, sodium bicarbonate or potassium bicarbonate, preferably sodium bicarbonate. The reaction is preferably carried out at 0° C. to room temperature in a two-phase mixture, preferably of water and a chlorinated hydrocarbon, such as, for example, methylene chloride or chloroform, in the presence of a phase transfer catalyst, such as, for example, tetrabutylammonium bisulfate.

Starting compounds of the formula III can also be prepared by halogen replacement. Thus, for example, a compound of the formula III in which X stands for iodine is obtained by reacting the corresponding compound III in which X stands for chlorine or bromine with an iodine salt, such as, for example, sodium iodide.

The preparation of the starting compounds of the general formula II is described in European patent 34,536.

The starting compounds of the general formula V with the activated carboxyl group are prepared in a manner which is known from the literature, and the esterification to give the compounds of the formula VI is carried out in the same manner as has been described for preparation of the esters of the general formula IV.

The compounds of the general formula VII can be prepared by processes which are known per se. Thus, for example, (compare European patent 134,420), diketene can be reacted with bromine and the resulting intermediate can then be reacted with a compound of the general formula VI, a preliminary product of the formula

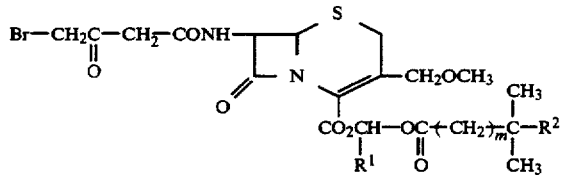

being obtained and substantially being converted by nitrosation (compare also European patent 134,420) into a compound of the general formula VII.

The ceph-3-em-4-carboxylic acid esters of the general formula I have a number of physicochemical and biological properties which make them useful cephalosporin antibiotics for oral administration. They are stable, colorless compounds which are readily soluble in the customary organic solvents, are absorbed in the intestine, are rapidly split in the serum to give the antibiotic cephalosporin derivative of the formula

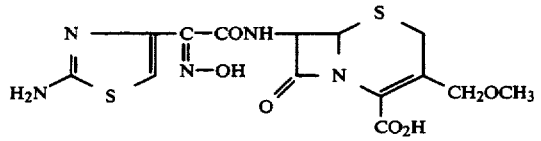

and are therefore outstandingly suitable for the treatment of bacterial infection diseases, such as, for example, infection of the respiratory tract or of the urogenital tract.

The compounds according to the invention are administered orally in the form of customary pharmaceutical formulations, for example, capsules, tablets, powders, syrups or suspensions. The dose depends on the age, symptoms and body weight of the patient and on the duration of treatment. However, it is as a rule between about 0.2 g and about 5 g per day, preferably between about 0.5 g and about 3 g per day. The compounds are preferably administered in divided doses, for example 2 to 4 times daily, and the individual dose can contain, for example, between 50 and 500 mg of active compound.

The oral formulations can contain the customary excipients and/or diluents. Thus, for example, binders, such as, for example, gelatin, sorbitol, polyvinylpyrrolidone or carboxymethyl cellulose, diluents, such as, for example, lactose, sugar, starch, calcium phosphates or polyethylene glycol, and lubricants, such as, for example, talc or magnesium stearate are possible for capsules or tablets, and aqueous or oily suspensions, syrups or similar known formulation forms, for example, are suitable for liquid formulations.

The following examples serve to further illustrate the invention, but do not limit it to them.

A. PREPARATION OF STARTING SUBSTANCE

Preparation Example 1

1-Chloroethyl chlorosulfate 18 ml of chlorosulfuric acid are added dropwise to 36 g of 1-chloroethyl chloroformate at 0° C. in the course of 15 minutes. The mixture is stirred vigorously until the evolution of gas has stopped (about 4 hours). It is poured onto 500 ml of ice-water/methylene chloride (1:1), the organic phase is separated off and the aqueous phase is extracted twice more with 150 ml of methylene chloride each time. The combined organic phases are washed twice with 300 ml of saturated sodium bicarbonate solution each time and once with 300 ml of saturated sodium chloride solution, dried over magnesium sulfate and concentrated and the residue is distilled in vacuo.

Boiling point (10): 49°-50° C.; yield 20 g.

Preparation Example 2 a) Methoxy Pivalic Acid

1st stage 8.8 g of sodium hydride suspension (60% strength) were suspended in 200 ml of dry dimethylformamide, and 29.2 g of ethyl hydroxypivalate were added slowly. The mixture was subsequently stirred for ½ hour and 28.4 g of methyl iodide in 40 ml of dimethylformamide were then added dropwise. After the mixture had been subsequently stirred at room temperature for one hour, it was poured onto 1,500 ml of ice-water and extracted with ether. The ether phases were washed several times with water, 1N hydrochloric acid and then with water, dried over sodium sulfate and evaporated on a rotary evaporator and the ester obtained was distilled in vacuo.

Boiling point (10):53°-55° C.; 53% yield

2nd stage 23.2 g of the ester from stage 1 were dissolved in 50 ml of methanol, 14.5 ml of 10N potassium hydroxide solution were added and the mixture was heated under reflux for 1 hour. After cooling, it was diluted with 50 ml of water and acidified to pH 2 with 2N hydrochloric acid. The solvent was removed on a rotary evaporator and the residue was extracted several times with ether. After the extract had been dried over sodium sulfate and the ether had been removed on a rotary evaporator, the resulting carboxylic acid was distilled in vacuo.

Boiling point (10):101°-105° C.; 64% yield.

The ethyl esters (stage 1) and carboxylic acids (stage 2) of the general formula

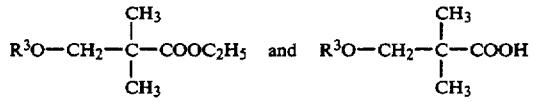

summarized in Table 1 were obtained analogously to preparation example 2a).

TABLE 1

| 2 | $R^3$ | % | Stage 1 boiling point | (mmHg) | % | Stage 2 boiling point | (mmHg) |
|---|---|---|---|---|---|---|---|
| b | $-C_2H_5$ | 33 | 70° | (13) | 68 | 110-6° | (10) |
| c | $-CH_2-CH=CH_2$ | 48 | 73-6° | (8) | 71 | 124 | (10) |
| d | $-C_4H_9$ | 32 | 95-8° | (9) | 74 | 82-7° | (0.4) |
| e | $-CH_2-C(CH_3)=CH_2$ | 54 | 79-88° | (8) | 84 | 138° | (10) |
| f | $-CH_2-C_6H_5$ | 55 | 132-8° | (8) | 98 | F. 71-2 | |

Preparation Example 3 a) 2,2-Dimethyl-3-phenylpropionic acid

Stage 1

Ethyl 2,2-dimethyl-3-phenylpropionate 25 ml of a 1.6M solution of n-butyllithium in n-hexane were added dropwise to a solution of 5.3 ml (7 g, 36 mmol) of ethyl bromoisobutyrate in 20 ml of tetrahydrofuran at −75° to −70° C. The mixture was then warmed to −20° C., 6.42 ml (9.43 g, 54 mmol) of benzylbromide were added dropwise and the mixture was subsequently stirred at room temperature for a further 3 hours. Dilute sulfuric acid was then added to the reaction mixture and the mixture was extracted twice with ether. The organic phase was washed with water, dried over magnesium sulfate and concentrated in vacuo. The crude product (6.6 g) was purified by distillation.

Yield: 4 g (57%) boiling point$_9$=115°-120° C.)

Stage 2

2,2-Dimethyl-3-phenylpropionic acid

A solution of 1 g (20 mmol) of ethyl 2,2-dimethyl-3-phenylpropionate (stage 1) and 3.5 g (61 mmol) of potassium hydroxide in 15 ml of methanol was heated under reflux for 2 hours. Thereafter, 50 ml of water were added and the mixture was extracted twice with ether. The aqueous phase was acidified with concentrated hydrochloric acid and extracted again with ether, the organic phase was dried over magnesium sulfate and the solvent was striped off in vacuo.

Yield: 2.4 g (70%)

$^1$H—NMR (60 MHz; $CDCl_3$): δ=(ppm) 1.2s, 6H 3.85, s, 2H 7.1, s, 5H.

The following compounds were obtained analogously to preparation example 3a:

b) 2,2-Dimethyl-4-pentynoic acid

Stage 1

Ethyl 2,2-dimethyl-4-pentynoate

Amounts used: 14.7 ml (0.1 m, 19.5 g) of bromoisobutyric acid, 75 ml of 1.6M n-butyllithium solution in n-hexane, 40 ml of tetrahydrofuran and 17.85 g of propargylbromide.

Yield: 11 g (72%)

Stage 2

2,2-Dimethyl-4-pentynoate

Amounts used: Crude product (stage 1) , 30 ml of methanol and 16.8 g (0.3 mm) of potassium hydroxide solution.

Yield: 7.3 g (58%) (boiling point$_{33}$=117° C.).

$^1$H—NMR ($CDCl_3$): δ(ppm)=10.1, br, s, 1H 2.46, d, 2H 2.03, t, 1H, 1.32, s, 6H Preparation Example 4 a) α-(Iodoethyl 2,2-dimethyl-propionate)

2.8 ml (50 mmol) of acetaldehyde in 10 ml of anhydrous acetonitrile were added dropwise to a solution of 7.5 g (50 mmol) of sodium iodide in 50 ml of anhydrous acetonitrile at 0° C. 6.2 ml (50 mmol) of 2,2-dimethylpropionyl chloride in 10 ml of acetonitrile were then added and the mixture was subsequently stirred at 0° C. for 2 hours. The yellowish solution was then poured onto 200 ml of ice-water and extracted with 250 ml of pentane. The organic phase was washed in each case once with water, 10% strength sodium bisulfite solution and saturated sodium chloride solution and dried over magnesium sulfate. After stripping off the solvent in vacuo (20° C. bath temperature), 7.9 g of a yellowish oil were obtained.

$^1$H—NMR (60 MHz, $CDCl_3$): δ (ppm): 1.25 (9H, s, tert.-butyl), 2.15 (3H, q, CH—$CH_3$), 6.8 (1H, q, CH—$CH_3$).

b) Iodomethyl 2,2-dimethylbutyrate 30 g (354 mmol) of sodium bicarbonate and then 3.1 g of tetrabutylammonium bisulfate were slowly added to a solution of 10.5 g (90 mmol) of 2,2-dimethylbutyric acid in 900 ml of a methylene chloride/water mixture (1+1). A solution of 18 g of chloromethyl chlorosulfonate in 100 ml of methylene chloride was then added dropwise and the two-phase mixture was subsequently stirred vigorously at +40° C. When the evolution of gas had ended (about 4.5 hours), the phases were separated, the aqueous solution was extracted twice with methylene chloride and dried over magnesium sulfate and the solvent was stripped off. 11.8 g (72%) of the chloromethyl ester were obtained.

$^1$H—NMR (60 MHz, $CDCl_3$): δ (ppm)=0.85 (3H, t, $CH_3CH_2$), 1.2 (6H, s, 2×$CH_3$), 1.5 (2H, q, $CH_2CH_3$), 5.7 (2H, s, $CH_2$—Cl).

11.6 g (71 mmol) of chloromethyl 2,2-dimethylbutyrate were dissolved in 150 ml of acetone, 12 g (80 mmol) of sodium iodide were added and the mixture was heated under reflux for 1 hour. It was then filtered, the filtrate was concentrated and the residue was taken up in ethyl acetate. The organic solution was washed successively with 5% strength sodium bisulfide solution and water and dried over magnesium sulfate. After the solvent had been stripped off, 12.4 g (68%) of the iodomethyl ester were obtained in the form of a Lemon-yellow oil which was further processed without additional purification.

The esters of the general formula

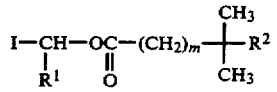

in which m is 0, summarized in Table 2 were obtained analogously to preparation examples 4a) and 4b).

TABLE 2

| 4 | $R^1$ | $R^2$ | % | Precursor to embodiment example |
|---|---|---|---|---|
| c* | H | $CH_3$ | 60 | 3 |
| d | H | $-CH=CH_2$ | 65 | 4 |
| e | H | $-CH_2-C\equiv CH$ | 60 | 14 |

TABLE 2-continued

| 4 | $R^1$ | $R^2$ | % | Precursor to embodiment example |
|---|---|---|---|---|
| f | $CH_3$ | $C_2H_5$ | 63 | 5 |
| g | H | $OC_2H_5$ | 85 | 7 |
| h | $CH_3$ | $OC_2H_5$ | 20 | 9 |
| | H | $OC_4H_9$ | 76 | 18 |
| k | $CH_3$ | $OC_4H_9$ | 71 | 20 |
| | H | $O—CH_2—CH=CH_2$ | 60 | 15 |
| m | H | $CH_2OCH_3$ | 65 | 6 |
| n | H | $CH_2OC_2H_5$ | 75 | 12 |
| o | $CH_3$ | $CH_2OC_2H_5$ | 33 | 8 |
| p | H | $CH_2OC_4H_9$ | 35 | 13 |
| q | $CH_3$ | $CH_2OC_4H_9$ | 41 | 19 |
| r | H | $CH_2OCH_2—CH=CH_2$ | 85 | 10 |
| s | $CH_3$ | $CH_2OCH_2—CH=CH_2$ | 30 | 11 |
| t | H | $CH_2OCH_2—C=CH_2$ $CH_3$ | 61 | 17 |
| u | H | $CH_2OCH_2C_6H_5$ | 63 | 16 |

*m = 1

Because of their high sensitivity, the ester were further reacted without being isolated.

Preparation Example 5

7-[2-(2-Tritylaminothiazol-4-yl)-2-(Z)-trityl-oximinoacetamido]-3-(methoxymethyl)-3-cephem-4-carboxylic acid Stage 1

2-(2-Tritylaminothiazol-4-yl)-2-(Z)-trityloximino-acetal chloride 46.5 g (60 mmol) of triethylammonium 2-(2-tritylaminothiazol-4-yl)-2-(Z)-trityloximino-acetate were dissolved in 400 ml of anhydrous methylene chloride and the solution was cooled to −70° C. A solution of 12.3 g (60 mmol) of phosphorus pentachloride in 200 ml of anhydrous methylene chloride was added dropwise so that the temperature did not rise above −60° C. The mixture was then subsequently stirred at this temperature for a further hour and the solution was thereafter concentrated directly in vacuo. In two further steps, in each case 100 ml of methylene chloride were added and mixture was evaporated on a rotary evaporator.

Stage 2

7-(2-(2-Tritylaminothiazol-4-yl)-2-(Z)-tritylox-iminoacetamido]-3-(methoxymethyl)-3-cephem-4-carboxylic acid A solution of the product from stage 1 in 50 ml of methylene chloride and 400 ml of acetone was added dropwise to a solution, cooled to 0° C., of 18 g of 7-amino-3-methoxymethyl-ceph-3-em-4-carboxylic acid in 400 ml of acetone/water (1:1), to which 5.6 g (66 mmol) of sodium bicarbonate and 18 ml (132 mmol) of triethylamine had first been added. After the mixture had stirred at 0° C. for 2 hours, it was brought to pH 4 with 1N hydrochloric acid and extracted with twice the amount of ethyl acetate. The phases were then separated and the organic solution was extracted with 5% strength potassium bisulfate solution. After drying over magnesium sulfate, the extract was concentrated, the residue was dissolved in 150 ml of methylene chloride and the solution was added dropwise to 1.8 l of diisopropyl ether, with vigorous stirring. After filtration with suction, 45.7 g (85%) of the title compound were obtained.

B. EMBODIMENT EXAMPLES 2,2-Dimethylbutanoyl-oxy-methyl 7-[2-(2-aminothiazol-4-yl)-2-(Z)-hydrox-yiminoacetamido]-3-(methoxymethyl)-3-cephem-4-carboxylate Process variant a)

Stage 1

2,2Dimethyl-butanoyloxy-methyl 7-[2-(2-tritylamino-thiazol-4-yl)-2-(Z)-trityl-oximinoacetamido]-3-(methoxymethyl)-3-cephem-4-carboxylate 1.07 g (7.7 mmol) of potassium carbonate were added to a solution of 14 g (15.6 mmol) of 7-[2-(2-tritylamino-thiazol-4-yl)-2(Z)-trityl-oximinoacetamido]-3-(methoxymethyl)-3-cephem-4-carboxylic acid in 300 ml of anhydrous dimethylformamide and the mixture was stirred at room temperature until the salt had dissolved. It was then cooled in an ice-bath and 4.9 g of iodomethyl 2,2-dimethylbutyrate were added. The mixture was subsequently stirred at 0° C. for a further 2 hours, the solvent was stripped off in vacuo and the residue was partitioned between ethyl acetate and water. The organic phase was dried over magnesium sulfate, the solution was concentrated and the solid residue was chromatographed ($SiO_2$: toluene/ethyl acetate=10+1). 4.6 g of pure title compound were obtained.

$^1H$—NMR (270 MHz, DMSO-$d_6$): δ (ppm)=0.75 (3H, t, $CH_2CH_3$) 1.15 (6H, s, $(CH_3)_2$), 1.53 (2H, m, $CH_2—CH_3$), 3.22 (3H, s, $OCH_3$), 3.57 (2H, AB, I=16 Hz, $SCH_2$), 4.18 (2H, s, $CH_2OCH_3$), 5.23 (1H, d, I=8 Hz, 6-H), 5.8–5.95 (3H, m, 7-H and $OCH_2O$), 6.58 (1H, s, thiazole-H), 7.15–7.35 (30H, m, aromatic H), 7.73 and 9.87 (2H, broad s and d, 2×NH).

Stage 2

2,2-Dimethyl-butanoyloxymethyl 7-[2-(2-amino-thiazol-4-yl)-2-(Z)-hydroxyimino-acetamido]-3-methoxymethyl)-3-cephem-4-carboxylate 4.5 g of the compound obtained in stage 1 were dissolved in 60 ml of formic acid at room temperature, 15 ml of water were added and the mixture was stirred at room temperature for 30 minutes. When the reaction had ended, the product was filtered off with suction, the solution was concentrated, toluene was added to the residue and the solvent was distilled off. The resinous residue was stirred in a mixture of diisopropyl ether/-diethyl ether. 2.0 g of the desired title compound were obtained.

$^1H$—NMR (270 MHz, DMSO-$d_6$): δ (ppm)=0.77 (3H, t, $CH_2CH_3$), 1.12 (6H, s, $CH_3$), 1.53 (2H, q, $CH_2CH_3$), 3.22 (3H, s, $OCH_3$), 3.56 (2H, AB, J=18 Hz, $SCH_2$), 4.14 (2H, s, $CH_2—OCH_3$), 5.18 (1H, d,J=6 Hz, 6-H), 5.82 (3H, m, 7-H and $—OCH_2—OCO—$), 6.66 (1H, s, thiazole-H), 7.10 (2H, broad s, $—NH_2$), .815 (1H, s, $HCO_2—$), 9.45 (1H, d, J=8 Hz, NH), 11.28 (1H, broad s, oxime-H).

Process variant b)

Precursor 2-(2-Tritylaminothiazol-4-yl)-2-(Z)-1-methyl-1-methoxy)-ethoxy-imino-acetic acid-p-toluenesulfonic acid anhydride 2.1 g (11 mmol) of p-toluenesulfonyl chloride were added to a suspension of 6 g (10 mmol) of triethylammonium 2-(2-tritylaminothiazol-4-yl)-2-(Z)-1-(methyl-1-methoxy)-ethoxyiminoacetate in 30 ml of acetone and the mixture was stirred at room temperature for 1.5 hours. 40 ml of diethyl ether were then added and the mixture was cooled to −10° C. and then filtered with suction. The product was rinsed three times more with 20 ml of ether each time and dried. 10 g of product which consisted of a mixture of the title compound and triethylamine hydrochloride and was further processed without additional purification were obtained.

Stage 1

2,2-Dimethyl-butanoyloxymethyl 7-[2-(2-Tritylaminothiazol-4-yl)-2-(Z)-(1-methyl-1-methoxy)ethoxyiminoacetamido-]-3-(methoxymethyl)-3-cephem-4-carboxylate 0.73 g (3 mmol) of 7-amino-3-methoxymethyl-ceph-3-em-4-carboxylate was suspended in 30 ml of methylene chloride, and 0.37 ml (2.4 mmol) of 1,8-diazabicyclo(5,4,0)-undec-7-ene (DBU) was added at 0° C. The solution formed was subsequently stirred for a further 30 minutes, 0.83 g (3.3 mmol) of iodomethyl 2,2-dimethylbutyrate (preparation example 4) was then added dropwise and the mixture was subsequently stirred at this temperature for 2 hours. 1.75 g (2.2 mmol) of the mixed anhydride obtained in the precursor stage was then added and the solution was kept at 0° C. for 1.5 hours.

When the reaction had ended, the solvent was stripped off in vacuo and the residue was chromatographed ($SiO_2$; toluene/ethyl acetate=1:1). 1.17 g (62%) of the desired compound were obtained.

$^1$H—NMR (270 MHz, DMSO-$d_6$): δ (ppm)=0.78 (3H, t, $CH_2CH_3$), 1.12 (6H, s, $(CH_3)_2$), 1.38 (6H, s, O—$C(CH_3)_2$), 1.52 (2H, q, $CH_2CH_3$), 3.10 (3H, s, $C(CH_3)_2$—$OCH_3$), 3.20 (3H, s, $OCH_3$), 3.57 (2H, AB, J=16 Hz, $SCH_2$—), 4.14 (2H, s, $CH_2$—$OCH_3$), 5.18 (1H, d, J=8 Hz, 6-H), 5.71 (1H, dd, 7-H), 5.85 (2H, AB, —$OCH_2$—O), 6.72 (1H, s, thiazole-H), 7.30 (15H, m, trityl-H), 8.84 (1H, s, —NH), 9.50 (1H, d, —NHCO).

Stage 2

2,2-Dimethyl-butanoyloxymethyl 7-[2-(2-aminothiazol-4-yl)-2-(Z)-hydroxyimino-acetamido-3-methoxymethyl)-3-cephem-4-carboxylate 1 g (1.2 mmol) of the compound obtained in stage 1 was dissolved in 15 ml of formic acid, and 3 ml of water were then added. After 1 hour at 0° C., the triphenylcarbinol formed was filtered off with suction and the filtrate was concentrated in vacuo. Toluene was added to the residue and the mixture was evaporated on a rotary evaporator again, this procedure being repeated several times. The crude produce was then taken up in ethyl acetate and extracted with saturated sodium bicarbonate solution and the organic phase was dried over magnesium sulfate and evaporated on a rotary evaporator. The residue was triturated with diethyl ether. 360 mg (60%) of the title compound, which is identical to the product obtained in process, a) in all its properties, were obtained.

Instead of the cephemcarboxylic acid ester, the tosylate thereof can also be used in stage 1 and can be prepared as follows. 1.5 ml (10 mmol) of 1,8-diazabicyclo-(5,4,0)undec-7-ene (DBU) were added to a suspension of 2.44 g (10 mmol) of 7-amino-3-methoxy-methyl-3-cephem-4-carboxylate in 100 ml of anhydrous methylene chloride and the solution formed was subsequently stirred at room temperature for 30 minutes. 2.6 g (10 mmol) of iodomethyl 2,2-dimethylbutyrate were then added dropwise at 0° C. and the mixture was subsequently stirred at room temperature for 1 hour. The mixture was concentrated, the residue was taken up in ethyl acetate and the mixture was extracted with aqueous sodium bicarbonate solution. The organic phase was dried with magnesium sulfate and the solvent was then stripped off in vacuo 3.0 g of crude product were obtained and were dissolved in 13 ml of ethyl acetate, and a solution of 1.8 g of p-toluenesulfonic acid in 13 ml of ethyl acetate was added, with stirring. Crystallization took place after a short time. The mixture was subsequently stirred for a further 10 minutes, 10 ml of diethyl ether were added, the mixture was filtered with suction and the residue was rinsed with a little ethyl acetate and diethylether to give 1.3 g of tosylate. Melting point=180° C. (decomposition).

$^1$H—NMR (270 MHz, DMSO-$d_6$); δ (ppm)=0.89 (3H, t, $CH_2CH_3$) 1.13 (6H, S, $(CH_3)_2$), 1.53 (2H, q, —$CH_2CH_3$), 2.29 (3H, s, $C_6H_5$—$CH_3$), 3.23 (2H, s, $OCH_3$), 3.7 (2H, J=20 Hz, S—$CH_2$), 4.21 (2H, s, $CH_2OCH_3$), 5.25 (2H, AB, J=10 Hz, —$OCH_2O$—), 5.83 and 5.9 (2H, 2×d, J=6 Hz, 6-H and 7-H), 7.13 and 7.47 (4H, 2×d, aromatic H).

Process variant c)

Precursor 1

2,2-Dimethyl-butanoyl-oxymethyl 7-amino-3-methoxymethyl-3-cephem-4-carboxylate 1.46 g (6 mmol) of 7-amino-3-methoxymethyl-3-cephem-4-carboxylate were suspended in 30 ml of methylene chloride, and 0.92 ml (6 mmol) of 1,8-diazabicyclo(5,4,0)-undec-7-ene (DBU) was added at 0° C. After 30 minutes, 1.66 g (6.5 mmol) of iodomethyl 2,2-dimethylbutyrate (compare preparation example 4) were added, while cooling with ice, and the mixture was subsequently stirred at room temperature for 2 hours. The precipitate which had separated out was filtered off with suction and the crude product was chromatographed ($SiO_2$; toluene/ethyl acetate=1:1). 1.2 g (53%) of the title compound were obtained.

$^1$H—NMR (270 MHz, DMSO-$d_6$): δ 0.8 (3H, t, $CH_2CH_3$) 1.1 (6H, s, $(CH_3)_2$), 1.52 (2H, q, $CH_2CH_3$), 3.2 (3H, s, $OCH_3$), 3.51 (2H, q, S—$CH_2$), 4.12 (2H, s, $CH_2OCH_3$), 4.8 (1H, m, 6H), 5.0 (1H, d, 7-H), 5.85 (2H, q, $OCH_2O$).

Precursor 2

2,2-Dimethyl-butanoyl-oxymethyl 7-(bromoacetylacetmamido)-3-methoxymethyl-3-cephem-4-carboxylate 0.16 ml (3.2 mmol) of bromine was added dropwise to a solution of 0.24 ml (3.2 mmol) of diketene in 20 ml of methylene chloride at −40° C. and the mixture was subsequently stirred for 30 minutes. Thereafter a solution of 1.2 g of the compound obtained in precursor 1 in 10 ml of methylene chloride was added dropwise. After 30 minutes, the solution was concentrated and the crude product was chromatographed ($SiO_2$; toluene acetate=1+1) to give 1.4 g of product.

Precursor 3

2,2-Dimethyl-butanoyl-oxymethyl 7(2-bromoacetyl-2-hydroxyimino-acetamido)-3-methoxymethyl-3-cephem-4-carboxylate A solution of 1.4 g (2.6 mmol) of the compound obtained in precursor 2 in 15 ml of methylene chloride and 8 ml of acetic acid was cooled to −10° C. and 284 mg (4.1 mmol) of sodium nitrite in 2 ml of water were added. After 30 minutes at room temperature, 252 mg (4.2mmol) of urea were added, and after 30 minutes 15 ml of water were added. The organic phase was separated off, washed several times with water and saturated sodium chloride solution and dried and the solvent was distilled off. 7.95 mg (54%) of the desired title compound were obtained.

$^1$H—NMR (270 MHz, DMSO-$d_6$); δ 0.78 (3H, t, $CH_2CH_3$), 1.12 (6H, s, $(CH_3)_2$), 1.53 (2H, q, $CH_2CH_3$), 3.20 (3H, s, $OCH_3$), 3.58 (2H, AB, J=15 Hz, S—$CH_2$), 4.14 (2H, s, $CH_2OCH_3$), 4.62 (2H, s, $BrCH_2$), 5.2 (1H, d, J=8 Hz, 6-H), 5.84 (3H, m, 7-H) and —$OCH_2$—), 9.36 (1H, d, NH), 11.15 (1H, s, oxime-H).

2,2-Dimethyl-butanoyloxymethyl 7-[2-(2-aminothiazol-4-yl-2-(Z)-hydroxyimino-acetamido-3-methoxymethyl)-3-cephem-4-carboxylate 0.14 g of thiourea was added to a solution of 0.79 g (1.4 mmol) of the compound obtained in precursor 3 in 5 ml of dimethylacetamide at 5° C. and the mixture was stirred at room temperature for 1 hour. 50 ml of a 3% strength sodium bicarbonate solution and 4 g of sodium chloride were then added to the solution and the precipitate which forms was filtered off with suction and taken up in 15 ml of ethyl acetate and 5 ml of acetone. The organic phase was washed with saturated sodium chloride solution and dried over magnesium sulfate, the solvent was stripped off and the residue was triturated with diethyl ether. 360 mg (47%) of the title compound which was identical to that obtained by process variants a) and b) were obtained.

Example 2

α-(2,2-dimethylpropionyloxy)-ethyl 7-[2-(2aminothiazol-4-yl)-2-(Z)-hydroxyiminoacetamido]-3-(methoxymethyl)-3-cephem-4-carboxylate Process variant a)

Stage 1

α-(2,2-Dimethyl-propionyloxy)-ethyl 7-[2-(2-tritylaminothiazol-4-yl)-2-(Z)-trityloximinoacetamido]-3-(methoxymethyl)-3-cephem-4-carboxylate 1.07 g (7.7 mmol) of potassium carbonate were added to a solution of 14 g (15.6 mmol) of 7-[2-(2-tritylaminothiazol-4-yl)-2-trityl-oximinoacetamido]-3-(methoxymethyl)-3-cephem-4-carboxylate in 300 ml of dimethylformamide and the mixture was stirred at room temperature until the salt had dissolved. Thereafter, if was cooled in an ice-bath and 5.1 g of iodoethyl α-2,2-dimethyl-propionate were added. The mixture was subsequently stirred at 0° C. for a further 2 hours, the solvent was stripped off in vacuo and the residue was partitioned between ethyl acetate and water. The organic phase was dried over magnesium sulfate, the solution was concentrated and the solid residue was chromatographed ($SiO_2$; toluene/ethyl acetate=10+1), 4.0 g of pure title compound were obtained in the form of a mixture of the two diastereomers.

$^1$H—NMR (270 MHz, $CDCl_3$); δ (ppm)=1.22 (9H, s, $C(CH_3)_3$), 1.55 (3H, d, $CH_3$), 3.3 (3H, s, $OCH_3$), 3.4 (2H, AB, J=16 Hz, $SCH_2$), 4.30 (2H, s, $CH_2OCH_3$), 5.05 (1H, d, 6-H), 6.08 (1H, m, 7-H), 6.4 (1H, broad s, thiazole-H), 6.9 (1H, q, OCH—$CH_3$), 7.1–7.4 (32H, 2×NH)

Stage 2

α-(2,2-Dimethylpropionyloxy)ethyl 7-[2-(2-aminothiazol-4-yl)-2-(Z)-hydroimino-acetamido]-3-methoxymethyl)-3-cephem-4-carboxylate 4.0 g of the compound obtained in stage 1 were dissolved in 60 ml of formic acid at room temperature, 15 ml of water were added and the mixture was stirred at room temperature for 30 minutes. When the reaction had ended, the mixture was filtered with suction, the solution was concentrated, toluene was added to the residue and the solvent was distilled off. The resinous residue was stirred in a mixture of diisopropyl ether/diethyl ether. 2.2 g of the desired title compound were obtained in the form of a mixture of the two diastereomers.

$^1$H—NMR (270 MHz, DMSO-$d_6$) δ (ppm)=1.15 (9H, 2×s, tert.-butyl), 1.5 (3H, dd, CH—$CH_3$), 3.2 (3H, 2×s, $OCH_3$), 3.55 (2H, m, S—$CH_2$—), 4.15 (2H, d, $CH_2$—$OCH_3$), 5.2 (1H, dd, J=6 Hz, H-6), 5.85 (1H, m, H-7), 6.65 (1H, s, thiazole-H), 6.9 (1H, m, —O—CH—O), 7.1 (2H, broad, s, $NH_2$), 9.45 (1H, d, J=8 Hz, —NH), 11.3 (1H, s, oxime-H)

Process variant b)

Precursor 2-(2-Tritylaminothiazol-4-yl)-(2-(Z)-(1-methyl-1-methoxy)-ethoxy-imino-acetic acid-p-toluenesulfonic acid anhydride 2.1 g (11 mmol) of p-toluenesulfonyl chloride were added to a suspension of 6 g (10 mmol) of triethylammonium 2-(2-tritylaminothiazol-4-yl)-2-(Z)-(1-methyl-1-methoxy)-ethoxyimino-acetate in 30 ml of acetone and the mixture was stirred at room temperature for 1.5 hours. 40 ml of diethyl ether were then added and the mixture was cooled to −10° C. and subsequently filtered with suction. The product was rinsed three times more with 20 ml of ether each time and dried. 10 g of product which consisted of a mixture of the title compound and triethylamine hydrochloride and was further processed without additional purification were obtained.

Stage 1

α-(2,2-Dimethylpropionyloxy)ethyl 7-[2-(2-tritylaminothiazol-4-yl)-2-(Z)-(1-methyl-1-methoxy)-ethoxyiminoacetamido-9 -3-(methoxymethyl)-3-cephem-4-carboxylate 0.73 g (3 mmol) of 7-amino-3-methoxymethyl-ceph-3-em-4-carboxylate was suspended in 30 ml of methylene chloride, and 0.37 ml (2.4 mmol) of 1,8-diazabicyclo(5,4,0)-undec-7-ene (DBU) was added at 0° C. The solution formed was subsequently stirred for a further 30 minutes, 0.79 g (3.3 mmol) of iodoethyl α-2,2-dimethylpropionate (preparation example 4) were then added dropwise and the mixture was subsequently stirred at this temperature for 2 hours. Thereafter, 1.9 g (2.4 mmol) of the mixed anhydride obtained in the precursor stage were added and this solution was kept at 0° C. for 1.5 hours.

When the reaction had ended, the solvent was stripped off in vacuo and the residue was chromatographed ($SiO_2$; toluene/ethyl acetate=1:1). 1.1 g (62%) of the desired compound were obtained in the form of a mixture of the two diastereomers.

$^1$H—NMR (270 MHz, DMSO-$d_6$) δ (ppm)=1.15 (9H, 2×s, tert.-butyl), 1.36 (6H, s, O—$C(CH_3)_2$), 1.51 (3H, dd, CH—$CH_3$) 3.1 (3H, s, $C(CH_3)_2$—$OCH_3$), 3.20 (3H, s, $OCH_3$), 3.58 (2H, AB, J=16 Hz, $SCH_2$—), 4–12 (2H, d, $CH_2OCH_3$), 5.18 (1H, AB, J=8 Hz, 6-H), 5.85 (1H, m, 7-H), 6.70 (1H, s, thiazole-H), 6.9 (1H, m, —O-CO—O), 7.15–7.4 (16H, m, aromatic H and NH), 9.5 (1H, d, —NHCO)

Stage 2

60-(2,2-Dimethylpropionyloxy)ethyl 7-[2-(2-aminothiazol-4-yl)-2-(Z)-hydroxyimino-acetamido]-3-(methoxymethyl)-3-cephem-4-carboxylate 1 (1.2 mmol) of the compound obtained in stage 1 was dissolved in 15 ml of formic acid, and 3 ml of water were then added. After 1 hour at 0° C., the triphenylcarbinol formed was filtered off with suction and the filtrate was concentrated in vacuo. Toluene was added to the residue and the mixture was evaporated again on a rotary evaporator, this procedure being repeated several times. The crude product was then taken up in ethyl acetate and extracted with saturated sodium bicarbonate solution and the organic phase was dried over magnesium sulfate and evaporated on a rotary evaporator. The residue was triturated with diethyl ether. 340 g (57%) of the title compound which is identical in all its properties to the product obtained in process variant a) were obtained.

Instead of the cephemcarboxylic acid ester, its tosylate can also be used in stage 1, this being prepared as follows:

1.5 ml (10 mmol) of 1,8-diazabicyclo-(5,4,0)-undec-7-ene (DBU) were added to a suspension of 2.44 g (10 mmol) of 7-amino-3-methoxymethyl-3-cephem-4-carboxylate in 100 ml of anhydrous methylene chloride and the solution formed was subsequently stirred at room temperature for 30 minutes. 2.6 g (10 mmol) of iodoethyl α-2,2-dimethyl-propionate were then added dropwise at 0° C. and the mixture was subsequently stirred at room temperature for 1 hour. It was concentrated, the residue was taken up in ethyl acetate and the mixture was extracted with aqueous sodium bicarbonate solution. The organic phase was dried with magnesium sulfate and the solvent was then stripped off in vacuo. 2.7 g of crude product were obtained and were dissolved in 13 ml of ethyl acetate, and a solution of 1.8 g of p-toluenesulfonic acid in 13 ml of ethyl acetate was added, with stirring. Crystallization took place after a short time. The mixture was subsequently stirred for a further 10 minutes, 10 ml of diethyl ether were added, the mixture was filtered with suction and the residue was rinsed with a little ethyl acetate and diethyl ether to give 1.0 g of tosylate. Melting point 160° C. (decomposition).

$^1$H—NMR (270 MHz, DMSO-$d_6$); δ (ppm)=1.15 (9H, s, tert.-butyl), 1.52 (3H, dd, CH—$CH_3$), 2.3 (3H, s, $C_6H_5$—$CH_3$), 3.25 (2H, s, $OCH_3$), 3.7 (2H, J=20 Hz, $SCH_2$—), 4.2 (2H, x, $CH_2OCH_3$), 5.75 (2H, 2×dd, 6-H and 7-H), 6.85 (1H, q, OCH—$CH_3$), 7.15 and 7.43 (4H, 2×d, aromatic H).

Process variant c)

Precursor 1

60-(2,2-Dimethyl-propionyloxy)-ethyl 7-amino-3-methoxymethyl-3-cephem-4-carboxylate 1.46 g (6 mmol) of 7-amino-3-methoxymethyl-3-cephem-4-carboxylate were suspended in 30 ml of anhydrous methylene chloride, and 0.9 ml (6 mmol) of 1,8-diazabicyclo-(5,4,0)-undec-7-ene (DBU) were added, while cooling with ice. After 30 minutes, 1.66 g (6.5 mmol) of iodoethyl α-2,2-dimethylpropionate were added dropwise and the mixture was subsequently stirred at room temperature for 2 hours. The residue which had precipitated was filtered off with suction and the crude product was chromatographed ($SiO_2$; toluene/ethyl acetate=1:1).

1.3 g (58%) of the title compound were obtained.

Precursor 2

α-(2,2-Dimethyl-propionyloxy)-ethyl 7-bromoacetylacetamido-3-methoxymethyl-3cephem-4-carboxylate 0.17 ml (3.5 mmol) of bromine was added dropwise to a solution of 0.26 ml (3.5 mmol) of diketene in 20 ml of anhydrous methylene chloride at −40° C. and the mixture was subsequently stirred for 30 minutes. Thereafter, a solution of 1.3 g of the compound obtained according to precursor 1 and 460 mg (3.5 mmol) of N-(trimethylsilyl)-acetamide in 10 ml of methylene chloride as added dropwise and after being stirred for 30 minutes the solution was concentrated. Chromatography of the crude product ($SiO_2$; toluene/ethyl acetate=1:1) give 0.9 g of product.

Precursor 3

α-(2,2-Dimethyl-propionyloxy)-ethyl 7-(2-bromoacetyl-2-hydroxyimino-acetamido)-3-methoxymethyl-3-cephem-4-carboxylate A solution of 0.9 g (1.7 mmol) of the compound obtained in precursor 2 in 10 ml of anhydrous methylene chloride and 5 ml of acetic acid was cooled to −10° C. and 182 mg (2.6 mmol) of sodium nitrite in 1.5 ml of water were added. After the mixture had been stirred at −5° C. for 30 minutes, 162 mg (2.7 mmol) of urea were then added and the mixture was subsequently stirred for 30 minutes. After addition of 10 ml of water, the organic phase was separated off, washed several times with water and saturated sodium chloride solution and dried and the solvent was distilled off. 580 mg (63%) of the title compound were obtained.

α-(2,2-Dimethyl-propionyloxy)-ethyl 7-[2-(2-aminothiazol-4-yl)-2-(Z)-hydroximino-acetamido]-3-methoxymethyl)-3-cephem-4-carboxylate 92 mg (1.2 mmol) of thiourea were added to a solution of 0.57 g (1 mmol) of precursor 3 in 5 ml of dimethylacetamide at 5° C. and the mixture was stirred at room temperature for 1 hour, 50 ml of a 3% strength sodium bicarbonate solution and 3.8 g of sodium chloride were then added to the solution and the precipitate formed was filtered off with suction and taken up in 15 ml of ethyl acetate and 5 ml of acetone. The organic phase was washed with saturated sodium chloride solution and dried over magnesium sulfate, the solvent was stripped off and the residue was triturated with diethyl ether to give 135 mg (24%) of the desired title compound, which was identical to that obtained by process variant a) or b).

EXAMPLE 2a

Separation of the diastereomers of α-(2,2-dimethylpropionyloxy)-ethyl 7-[2-(2-aminothiazol-4-yl)-2-(Z)-hydroxyimino-acetamido]-3-(methoxymethyl)-3-cephem-4-carboxylate Stage 1

Pure diastereomers of α-(2,2-dimethylpropionyloxy)-ethyl 7-[2-(2-tritylaminothiazol-4-yl)-2-(Z)-(1-methyl-1-methoxy)-ethoxyaminoacetamido]-3-(methoxymethyl)-3-cephem-4-carboxylate 3 ml (20.3 mmol) of 1,8-diazabicyclo-(5,4,0)-undec-7-ene (DBU) were added dropwise to a solution of 14.8 g (20.3 mmol) of 7-[2-(2-tritylaminothiazol-4-yl)-2-(Z)-(1-methyl-1-methoxy)-ethoxyiminoacetamido]-3-(methoxymethyl)-3-cephem-4-carboxylic acid in 100 ml of anhydrous methylene chloride. The solution was subsequently cooled to 0° C., and 6.7 g (26.4 mmol) of iodoethyl α-2,2-dimethyl-propionate were added. The mixture was subsequently stirred at 0° C. for a further 2 hours, the solvent was subsequently stripped off in vacuo and the residue was partitioned between ethyl acetate and water. The organic phase was dried over magnesium sulphate, the solution was concentrated, and the solid residue (19.1 g), which contained a mixture of the two diastereomers, was chromatographed (900 g of $SiO_2$; toluene/ethyl acetate=5+1; after elution of the first diastereomers toluene/ethyl acetate=4+1). In this manner, 2.8 g of the first diastereomer (RF value=0.75; toluene/ethyl acetate 1+1) and 3.2 g of the other diastereomer (RF value=0.7) are obtained in uniform form.

Stage 2

Pure diastereomers of α-(2,2-dimethyl-propionyloxy)-ethyl 7-[2-(2-aminothiazol-4-yl)-2-(Z)-hydroxyiminoacetamido]-3-(methoxymethyl)-3-cephem-4-carboxylate Each of the two diastereomers obtained in stage 1 was dissolved in 10 ml of formic acid, 2.5 ml of water were added, and the mixture was stirred at room temperature for 1 hour. The triphenylcarbinol formed was subsequently filtered off with suction, and the filtrate was concentrated in vacuo. The residue was subsequently taken up on 100 ml of ethyl acetate, the solution was extracted with saturated sodium hydrogen carbonate solution, the organic phase was dried over magnesium sulfate, and the solvent was stripped off in vacuo. The residue was triturated with diisopropyl ether. For further purification, the product was crystallized from n-butyl acetate/diisopropylamine.

Diastereomer I: 1.2 g from 2.8 g of stage 1, m.p. = from 166° C. (decomposition)

$^1$H—NMR (270 MHz, DMSO-dg); δ (ppm) = 1.15 (9H, s, tert.-butyl), 1.46 (3H, d, CH—$CH_3$), 3.19 (3H, s, $OCH_3$), 3.56 (2H, AB system, J = 6Hz, S—$CH_2$), 4.15 (2H, d, $CH_2OCH_2$), 5.21 (1H, d, J = 6 Hz, M-6), 5.83 (1H, m, H-7), 6.64 (1H, s, thiazol-H), 6.87 (1H, q, —O—CH—O), 7.1 (2H, broad s, $NH_2$), 9.5 (1H, d, J = 8 Hz, —NH), 11.3 (1H, s, oxime-H).

Diastereomer II: 1 g from 3.2 g of stage 1, m.p. = from 138° C. (decomposition)

$^1$H—NMR (270 MHz, DMSO-$d_6$); δ (ppm) = 1.15 (9H, s, tert.-butyl), 1.47 (3H, d, CH—$CH_3$), 3.2 (3H, s, $OCH_3$), 3.54 (2H, ABsystem, J = 6 Hz, S—$CH_2$—), 4.13 (2H, s, $CH_2$—$OCH_3$), 5.19 (1H, d, J = 6 Hz), H-6), 5.82 (1H, m, H-7), 6.64 (1H, s, thiazole-H), 6.93 (1H, 1, —O—CH—O), 7.1 (2H, broad s, $NH_2$), 9.45 (1H, d, J = 8 Hz, —NH), 11.3 (1H, s, oxime-H).

The compounds of the formula I

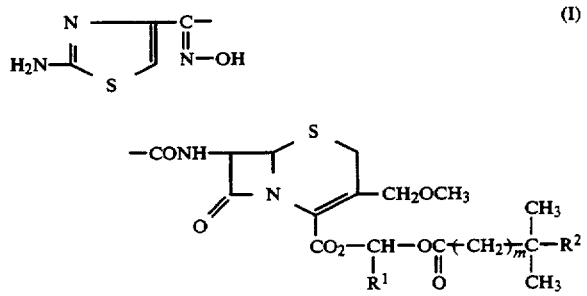

(I)

Listed in Table 3 were obtained as amorphous solids analogously to Examples 1 and 2, process variants a), b) or c).

TABLE 3

| Example No | m | $R^1$ | $R^2$ | $^1$H-NMR (270 MHz, DMSO-$d_6$), δ (ppm) = |
|---|---|---|---|---|
| 3 | 1 | H | $CH_3$ | 1.05(9H, s, $(CH_3)_3$), 2.25(2H, s, $\underline{CH_2}$—'Bu), 3.2(3H, s, $OCH_3$, 3.55(2H, AB, J = 16 Hz, S$\underline{CH_2}$) 4.15(2H, s, $\underline{CH_2}OCH_3$), 5.20(1H, d, J = 6 Hz, 6-H), 5.85(3H, m, 7-H and O$\underline{CH_2}$O), 6.15(1H, s, Thiazole-H), 7.1(2H, broad s, $NH_2$), 9.45(1H, d, NH), 11.25(1H, broad s, Oxime-H) |
| 4 | 0 | H | —CH=$CH_2$ | 1.27(6H, s, $CH_3$), 3.20(3H, s, $OCH_3$), 3.60(2H, AB, J = 16 Hz, s-$CH_2$), 4.15(2H, s, $\underline{CH_2}$—$OCH_3$), 5.1-5.2(2H, m, 6-H, $\underline{CH}$=$CH_2$), 6.65(1H, s, Thiazole-H), 7.10(2H, broad s, $NH_2$), 9.47(1H, broad s, NH), 11.25(1H, s, oxime-H) |
| 5 | 0 | $CH_3$ | —$CH_2$—$CH_3$ | 0.78(3H, t, $CH_2$—$\underline{CH_3}$), 1.10(6H, s, $CH_3$), 1.50(5H, m), 3.21(3H, s, $OCH_3$), 3.50 (2H, AB, J = 16 Hz, S—$CH_2$), 4.12(2H, s $\underline{CH_2}$—$OCH_3$), 5.18(1H, d, J = 8 Hz, 6-H), 5.83(1H, dd, J = 8 Hz, 7-H), 6.65(1H, s, Thiazole-H), 6.90(1H, m, —O$\underline{CH}$—O), 7.10(2H, broad, s, $NH_2$), 9.45(1H, borad s, NH), 11.28(1H, broad s, oxime-H) |
| 6 | 0 | H | —$CH_2OCH_3$ | 1.1(6H, s, 2×$CH_3$), 3.2(6H, s, $OCH_3$), 4.15(2H, s, $\underline{CH_2}$—$OCH_3$), 5.20(1H, d, J = 6 Hz, 6-H), 5.75(1H, dd, 7-H), 5.85(2H, AB, —O$\underline{CH_2}$—O—), 6.7(1H, broad s, Thiazole-H), 9.5(1H, d, NH), 11.5(1H, s, oxime-H) |
| 7 | 0 | H | —$OC_2H_5$ | 1.1(3H, t, $OCH_2\underline{CH_3}$), 1.35(6H, s, $CH_3$), 3.2(3H, s, $OCH_3$), 3.85(2H, q, O$\underline{CH_2}CH_3$), 4.15(2H, s, $\underline{CH_2}$—$OCH_3$), 5.2(1H, d, J = 6 Hz, 6-H), 5.8(1H, dd, 7-H), 5.9(2H, AB, —O$\underline{CH_2}$O—), 6.65(1H, s, Thiazole-H), 7.10(2H, broad s, $NH_2$), 9.45(1H, d, NH), 11.3(1H, s, oxime-H) |
| 8 | 0 | $CH_3$ | —$CH_2OC_2H_5$ | 1.1(3H, 2×t, $OCH_2\underline{CH_3}$), 1.15(6H, 2×s, $CH_3$), 1.45(3H, 2×d, CH$\underline{CH_3}$), 3.2 (3H, 2×s, $OCH_3$), 4.1(2H, d, $\underline{CH_2}OCH_3$), 5.2(1H, 2×d, 6-H), 5.85(1H, dd, 7-h), 6.7(1H, s, Thiazole-H), 6.9(1H, 2×q, O$\underline{CH}$—O), 7.10(2H, broad s, $NH_2$), 9.5(1H, 2 ×d, NH), 11.4(1H, broad s, oxime-H) |
| 9 | 0 | $CH_3$ | —$OC_2H_5$ | 1.5(3H, 2×d, CH—$\underline{CH_3}$), 3.25(3H, 2×s, $CH_2O\underline{CH_3}$), 4.1(2H, s, $\underline{CH_2}OCH_3$), 5.2 (1H, 2×d, H-6), 5.7(1H, 2×dd, H-7), 6.7(1H, 2×s, Thiazole-H), 6.9(1H, 2×q, O—$\underline{CH}$—O), 7.25(2H, broad s, $NH_2$), 9.5(1H, d, NH), 11.4(1H, s, oxime-H) |
| 10 | 0 | H | —$CH_2O$—$CH_2$—CH=$CH_2$ | 1.15(6H, s, $CH_3$), 3.4(2H, s, Alkyl$\underline{CH_2}$—O), 4.15(2H, s, $\underline{CH_2}$—$OCH_3$), 5.15(2H, m, olefinic H), 5.25(2H, d, H-6), 5.8(1H, dd, 7-H), 5.85(3H, m, olefinic H and O$\underline{CH_2}$O), 6.65(1H, broad s, Thiazole-H), 7.25(2H, broad s, $NH_2$), 9.45(1H, d, NH), 11.3(1H, broad s, oxime-H) |
| 11 | 0 | $CH_3$ | —$CH_2O$—$CH_2$—CH=$CH_2$ | 1.45(3H, 2×d, CH—$\underline{CH_3}$), 3.2 Alkyl(3H, 2×s, $OCH_3$), 3.4(2H, s, $\underline{CH_2}$O), 3.5 (2H, AB, J = 16 Hz, S—$CH_2$), 4.15(2H, 2×s, $\underline{CH_2}OCH_3$), 5.15(2H, m, CH=$\underline{CH_2}$), 5.25(1H, d, J = 6 Hz, H-6), 5.8(1H, dd, J = 6 Hz, 7-Hz, 5.85(1H, m, olefinic H and O$\underline{CH_2}$O), 6.65(1H, s, Thiazole-H), 6.9(1H, 2×q, O$\underline{CH}$—O), 7.20 (2H, broad s, $NH_2$), 9.45(1H, 2×d, NH), 11.3(1H, s, oxime-H) |

TABLE 3-continued

| Example No | m | $R^1$ | $R^2$ | $^1$H-NMR (270 MHz, DMSO-$d_6$), δ (ppm) = |
|---|---|---|---|---|
| 12 | 0 | H | $-CH_2OC_2H_5$ | 1.05(3H, t, $CH_2CH_3$), 1.15(6H, s, $CH_3$), 3.2(3H, s, $OCH_3$), 3.35(2H, broad s, C—$\underline{CH_2}$—O—), 3.4(2H, q, —O—$\underline{CH_2}$—$CH_3$), 3.55(2H, AB, J=16 Hz, S—$\underline{CH_2}$), 4.15(2H, broad s, $\underline{CH_2}$—$OCH_3$), 5.2(1H, d J=6 Hz, H-6), 5.85(3H, m, H-7 and —$\underline{CH_2}$—OCO), 6.65(1H, s, Thiazole-H), 7.1(2H, s, $NH_2$), 9.45(1H, d, J=8 Hz, NH), 11.3(1H, s, oxime-H) |
| 13 | 0 | H | $-CH_2OC_4H_9$ | 0.85(3H, t, J=7 Hz, —$CH_2$—$\underline{CH_3}$), 1.15(6H, s, $C(CH_3)_2$), 1.25 and 1.45 (together 4H, m, —$\underline{CH_2}$—$\underline{CH_2}$—), 3.2(3H, s, $OCH_3$), 3.35(4H, —C—$\underline{CH_2}$—O— and —O—$\underline{CH_2}CH_3$—), 3.55(2H, AB, J=16 Hz, S—$\underline{CH_2}$—), 4.15(2H, s, $\underline{CH_2}OCH_3$), 5.2(1H, d, J=6 Hz, H-6), 5.85(3H, m, H-7 and —$\underline{CH_2}$OCO—), 6.65(1H, s, Thiazole-H), 7.1(2H, broad s, $NH_2$), 9.45(1H, d, J=8 Hz, —NH), 11.3(1H, s, oxime-H) |
| 14 | 0 | H | $-CH_2-C\equiv CH$ | 1.22(6H, s, 2×$CH_3$), 2.43(2H, d, —$CH_2$—C≡CH, 2.87(1H, t, —$CH_2$—C≡CH), 3.22(3H, s, $OCH_3$), 3.56(2H, AB, J=16 Hz, —S—$CH_2$), 4.15(2H, s, $CH_2$—$OCH_3$), 5.2(1H, d, J=6 Hz, H-6), 5.85(3H, H-7 and —$CH_2$—OCO), 6.65(1H, s, Thiazole), 7.1(2H, s, $NH_2$), 9.45(1H, d, J=8 Hz, NH), 11.3(1H, s, oxime-H) |
| 15 | 0 | H | $-O-CH_2CH=CH_2$ | 1.4(6H, s, 2×$CH_3$), 3.2(3H, s, $OCH_3$), 3.55(2H, AB, J=16 Hz, —S—$CH_2$), 3.9 (2H, m, $OCH_2CH$—, 4.15(2H, s, $CH_2$—$OCH_3$), 5.15(2H, m, =$CH_2$), 5.2(1H, d, J=6 Hz, H-6), 5.85(4H, m, —CH=, H-7 and —$CH_2$OCO), 6.65(1H, s, Thiazole), 7.1(2H, s, $NH_2$), 9.45(1H, d, NH), 11.3(1H, s, oxime-H) |
| 16 | 0 | H | $-CH_2-OCH_2C_6H_5$ | 1.15(6H, s, 2×$CH_3$), 3.2(3H, s, $OCH_3$), 3.45(2H, s, —$CH_2$O—), 3.55(2H, AB, J=16 Hz, —S$CH_2$—), 4.1(2H, AB, $CH_2OCH_3$), 4.45(2H, s, $CH_2$O-Benzyl), 5.15 (1H, d, J=6 Hz, H-6), 5.85(3H, m, H-7 and —$OCH_2$O—), 6.65(1H, s, Thiazole), 7.1(2H, s, $NH_2$), 7.35(5H, m, arom. H), 9.45(1H, d, NH), 11.3(1H, s, oxime-H) |
| 17 | 0 | H | $-CH_2-OCH_2-C(CH_3)=CH_2$ | 1.15(6H, s, 2×$CH_3$), 1.65(3H, s, $CH_3$), 3.2(3H, s, $OCH_3$), 3.35(2H, s, $CH_2$—O—), 3.55(2H, AB, J=16 Hz, —S—$CH_2$), 3.8(2H, s, —$OCH_2$—CH—), 4.15(2H, s, $CH_2OCH_3$), 4.85(2H, d, J=12 Hz, =$CH_2$), 5.2(1H, d, J=6 Hz, H-6), 5.85(3H, m, H-7 and —$CH_2$OCO), 6.65(1H, s, Thiazole), 7.1(2H, s, $NH_2$), 9.45(1H, d, NH), 11.3 (1H, s, oxime-H) |
| 18 | 0 | H | $-OC_4H_9$ | 0.85(3H, t, J=7 Hz, —$CH_2CH_3$), 1.3 and 1.45(4H, 7 Hz, —$CH_2$—$CH_2$—$CH_3$), 1.35(6H, s, 2×$CH_3$), 3.2(3H, s, $OCH_3$), 3.35(2H, q, J=7 Hz, $CH_2$), 3.55(2H, AB, J=16 Hz, —S—$CH_2$), 4.15(2H, s, $CH_2OCH_3$), 5.2(1H, d, J=6 Hz, H-6), 5.85 and 5.9(3H, q and AB, J=6 Hz, H-7 and $CH_2$OCO), 6.65(1H, s, thiazole), 7.1(2H, s, $NH_2$), 9.45(1H, d, J=8 Hz, NH), 11.3(1H, s, oxime-H) |
| 19 | 0 | $CH_3$ | $-CH_2OC_4H_9$ | 0.85(3H, t, J=7 Hz, $CH_2$—$CH_3$), 1.1(6H, s, 2×$CH_3$), 1.3(2H, q, J=7 Hz, $CH_2CH_3$), 1.45(5H, 2×d and q, J=6 Hz, $CHCH_3$ and $CH_2$), 3.2(3H, 2×s, $OCH_3$), 3.35(4H, $CH_2$—$OCH_2$), 3.5(2H, 2×AB, —$SCH_2$), 4.15(2H, 2×s, $CH_2$—$OCH_3$), 5.2(1H, 2×d, H-6), 5.85(1H, 2×q, J=5 Hz, H-7), 6.9(1H, 2×q, J=6 Hz, $CHCH_3$), 7.1(2H, s, $NH_2$), 9.45(1H, 2×d, J=8 Hz, NH), 11.3(1H, s, oxime-H) |
| 20 | 0 | $CH_3$ | $-OC_4H_9$ | 0.85(3H, t, J=7 Hz, $CH_2CH_3$), 1.35(6H, s, 2×CH), 1.45 and 1.5(7H, m, $CHCH_3$, 2×$CH_2$), 3.2(3H, s, $OCH_3$), 3.3(2H, m, $OCH_2CH_2$—), 3.55(2H, m, —$SCH_2$), 4.15 (2H, 2×s, $CH_2OCH_3$), 5.2(1H, pseudo-t, J=7 Hz, H-6), 5.85(1H, 2×q, J=5 Hz, H-7), 6.7(1H, s, Thiazole), 6.9(1H, 2×q, CH—$CH_2$), 7.35(2H, s, $NH_2$), 9.5(1H, 2×d, NH), 11.5(1H, s, oxime-H) |

We claim:

1. [A cephemcarboxylic acid ester of the formula I

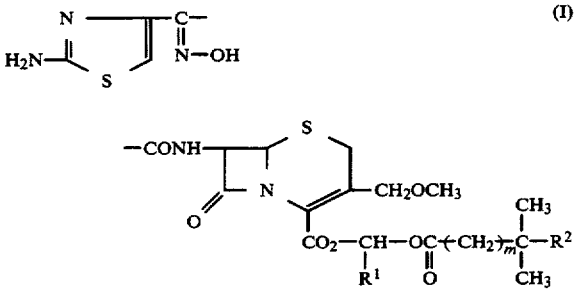

(I)

in which m denotes 0 or 1, $R^1$ denotes hydrogen or methyl and $R^2$ denotes $C_1$–$C_6$-alkyl, $C_2$–$C_6$-alkenyl, $C_2$–$C_6$-alkynyl or the group $$-(CH_2)_n-OR^3$$

in which n stands for 0 or 1 and $R^3$ has the meaning of $C_1$–$C_6$-alkyl, which can also be further substituted by phenyl, or of $C_3$–$C_4$-alkenyl, in which the HO group is in the syn-position and, if m is 0 and $R^1$ is hydrogen, $R^2$ cannot be methyl physiologically tolerated acid addition salts thereof or their diastereomers] *A compound consisting essentially of pure diastereomer I of α-(2,2-dimethyl-propionyloxy)-ethyl 7-[2-(2-aminothiazol-4-yl)-2-(Z)-hydroxyimino-acetamido]-3-(methoxymethyl)-3-cephem-4-carboxylate or a physiologically tolerated acid addition salt thereof.*

[2. A cephemcarboxylic acid ester as claimed in claim 1, in which $R^1$ and the meaning given there and $R^2$ stands for $C_1$–$C_4$-alkyl, $C_2$–$C_4$-alkenyl, $C_3$–$C_4$-alkynyl or the group $$-(CH_2)_n-OR^3$$

in which n is 0 or 1 and $R^3$ has the meaning of $C_1$–$C_4$-alkyl, which can also be further substituted by phenyl, or of $C_3$–$C_4$-alkenyl.]

[3. 2,2-Dimethyl-butanoyl-oxymethyl 7-[2-(2-aminothiazol-4-yl)-2-(Z)-hydroxyimino-acetamido]-3-(methoxymethyl)-3-cephem-4-carboxylate.]

[4. 2,2-Dimethyl-3-butenoyl-oxymethyl 7-[2-(2-aminothiazol-4-yl)-2-(Z)-hydroxyimino-acetamido]-3-(methoxymethyl)-3-cephem-4-carboxylate.]

[5. α-(2,2-Dimethyl-butanoyloxy)-ethyl 7-[2-(2-aminothiazol-4-yl)-2-(Z)-hydroxyimino-acetamido]-3-(methoxymethyl)-3-cephem-4-carboxylate.]

[6. α-(2,2-Dimethyl-propionyloxy)-ethyl 7-[2-(2-aminothiazol-4-yl)-2-(Z)-hydroxyimino-acetamido-9-3-(methoxymethyl)-3-cephem-4-carboxylate and its diastereomers.]

7. A pharmaceutical formulation which is active against bacterial infections, [which contains a cephemcarboxylic acid ester of the formula I as claimed in claim 1 together with a pharmaceutically acceptable carrier] *comprising a pharmaceutically acceptable carrier and a compound consisting of essentially of pure diastereomer I of α-(2,2-dimethylpropionyloxy)-ethyl 7-[2-(2-aminothiazol-4-yl)-2-(Z)-hydroxyimino-acetamido]-3-(methoxymethyl)-3-cephem-4-carboxylate or a physiologically tolerated acid addition salt thereof.*

8. A method of combating bacterial infections which comprises administering *to an animal host in recognized need thereof* an effective amount of [a cephemcarboxylic acid ester of the formula I as claimed in claim 1] *a compound consisting essentially of pure diastereomer I of α-(2,2-dimethyl-propionyloxy)-ethyl 7-[2-(2-aminothiazol-4-yl)-2-(Z)-hydroxyimino-acetamido]-3-(methoxymethyl)-3-cephem-4-carboxylate or a physiologically tolerated acid addition salt thereof.*

[9. A cephemcarboxylic acid as claimed in claim 1, in which m denotes O, $R^1$denotes hydrogen or methyl and $R^2$ denotes $C_1$–$C_4$ alkyl.]

[10. A cephemcarboxylic acid as claimed in claim 1, in which m denotes O, $R^1$ denotes hydrogen or methyl and $R^2$ denotes methyl or ethyl.]

[11. A cephemcarboxylic acid as claimed in claim 1, in which m denotes O, $R^1$methyl and $R^2$denotes methyl.]

* * * * *